(12) United States Patent
Streibig et al.

(10) Patent No.: US 9,946,335 B1
(45) Date of Patent: Apr. 17, 2018

(54) DISPLAY APPARATUS INCLUDING A TRANSPARENT ELECTRONIC MONITOR

(71) Applicant: Iontank, Ltd., Pittsburgh, PA (US)

(72) Inventors: Stephen Streibig, Pittsburgh, PA (US); Robert de la Cretaz, Pittsburgh, PA (US)

(73) Assignee: IONTANK, LTD., Pittsburgh, PA (US)

( * ) Notice: Subject to any disclaimer, the term of this patent is extended or adjusted under 35 U.S.C. 154(b) by 37 days.

(21) Appl. No.: 15/168,843

(22) Filed: May 31, 2016

Related U.S. Application Data

(62) Division of application No. 14/068,920, filed on Oct. 31, 2013, now Pat. No. 9,635,305.

(Continued)

(51) Int. Cl.
| | |
|---|---|
| *H04N 5/00* | (2011.01) |
| *G06F 3/01* | (2006.01) |
| *G02F 1/137* | (2006.01) |
| *A01K 1/03* | (2006.01) |
| *A01K 29/00* | (2006.01) |

(Continued)

(52) U.S. Cl.
CPC .............. *G06F 3/011* (2013.01); *A01K 1/031* (2013.01); *A01K 29/005* (2013.01); *A01K 31/06* (2013.01);

(Continued)

(58) Field of Classification Search
CPC ............ H04N 5/64; G01S 3/046; G01F 19/00

(Continued)

(56) References Cited

U.S. PATENT DOCUMENTS

| | | |
|---|---|---|
| 2002/0046100 A1 | 4/2002 | Kinjo |
| 2006/0164725 A1 | 7/2006 | Horsten et al. |

(Continued)

FOREIGN PATENT DOCUMENTS

| | | |
|---|---|---|
| EP | 1208776 A1 | 5/2002 |
| JP | 2005187061 A | 7/2005 |

OTHER PUBLICATIONS

Planar LookThru Transparent LCD Display, Planar Systems, Inc., 2012.

(Continued)

*Primary Examiner* — Jeffery Williams
(74) *Attorney, Agent, or Firm* — William F. Lang IV; Lang Patent Law LLC

(57) ABSTRACT

A display apparatus includes a transparent electronic display such as a non-backlit LCD screen, a display area disposed behind the transparent electronic display, and a light source for illuminating the display area. When the light source is activated, the pixels of the LCD screen, and objects behind the screen, become visible. Various examples of the display apparatus include additional enhancements to the visual image and/or functionality. These enhancements include additional monitors for coordinated displays, user-controlled turntables with coordinated informational displays, parallax compensation, RFID sensors for identifying objects to be displayed, and switchable liquid crystal films and/or polarized mirror coatings to further control revealing and concealing of objects behind the screen. Some examples of the display apparatus may include an animal habitat. The animal habitat may be selectively revealed or concealed. The display apparatus may incorporate screen displays with animal movements for unique visual effects.

13 Claims, 16 Drawing Sheets

Related U.S. Application Data

(60) Provisional application No. 61/722,155, filed on Nov. 3, 2012.

(51) Int. Cl.
  *A01K 63/00* (2017.01)
  *A01K 31/06* (2006.01)
  *A01K 67/033* (2006.01)

(52) U.S. Cl.
  CPC .......... *A01K 63/003* (2013.01); *A01K 67/033* (2013.01); *G02F 1/137* (2013.01); *A01K 2227/10* (2013.01); *A01K 2227/30* (2013.01); *A01K 2227/40* (2013.01); *A01K 2227/706* (2013.01)

(58) Field of Classification Search
  USPC ........................................................ 348/143
  See application file for complete search history.

(56) References Cited

U.S. PATENT DOCUMENTS

| | | |
|---|---|---|
| 2008/0049189 A1 | 2/2008 | Vrachan et al. |
| 2008/0192027 A1 | 8/2008 | Morrison |
| 2010/0002175 A1 | 1/2010 | Kim et al. |
| 2011/0102703 A1 | 5/2011 | Moon et al. |
| 2011/0128386 A1 | 6/2011 | Letessier et al. |
| 2011/0163986 A1 | 7/2011 | Lee et al. |
| 2011/0170170 A1* | 7/2011 | Boote ............... B32B 17/10174 359/296 |
| 2012/0038868 A1 | 2/2012 | Jun et al. |
| 2012/0112225 A1 | 5/2012 | Le Bellac et al. |
| 2012/0120007 A1 | 5/2012 | Choi et al. |
| 2012/0242865 A1* | 9/2012 | Vartanian ........... H04N 5/23206 348/239 |
| 2014/0144083 A1* | 5/2014 | Artwohl ................ A47F 3/0434 49/70 |
| 2014/0210322 A1 | 7/2014 | Roberts et al. |

OTHER PUBLICATIONS

Sightlines: Augmenting an Object with Face-Tracking and Reactive Content, Second Story Studios, Sep. 10, 2012, http://blog.secondstory.com/sightlines-augmenting-an-objec.

Primeview 22 inch transparent LCD monitor.

Crystal Display Systems website, http://crystal-display.com/digital-signage/clearvue/.

* cited by examiner

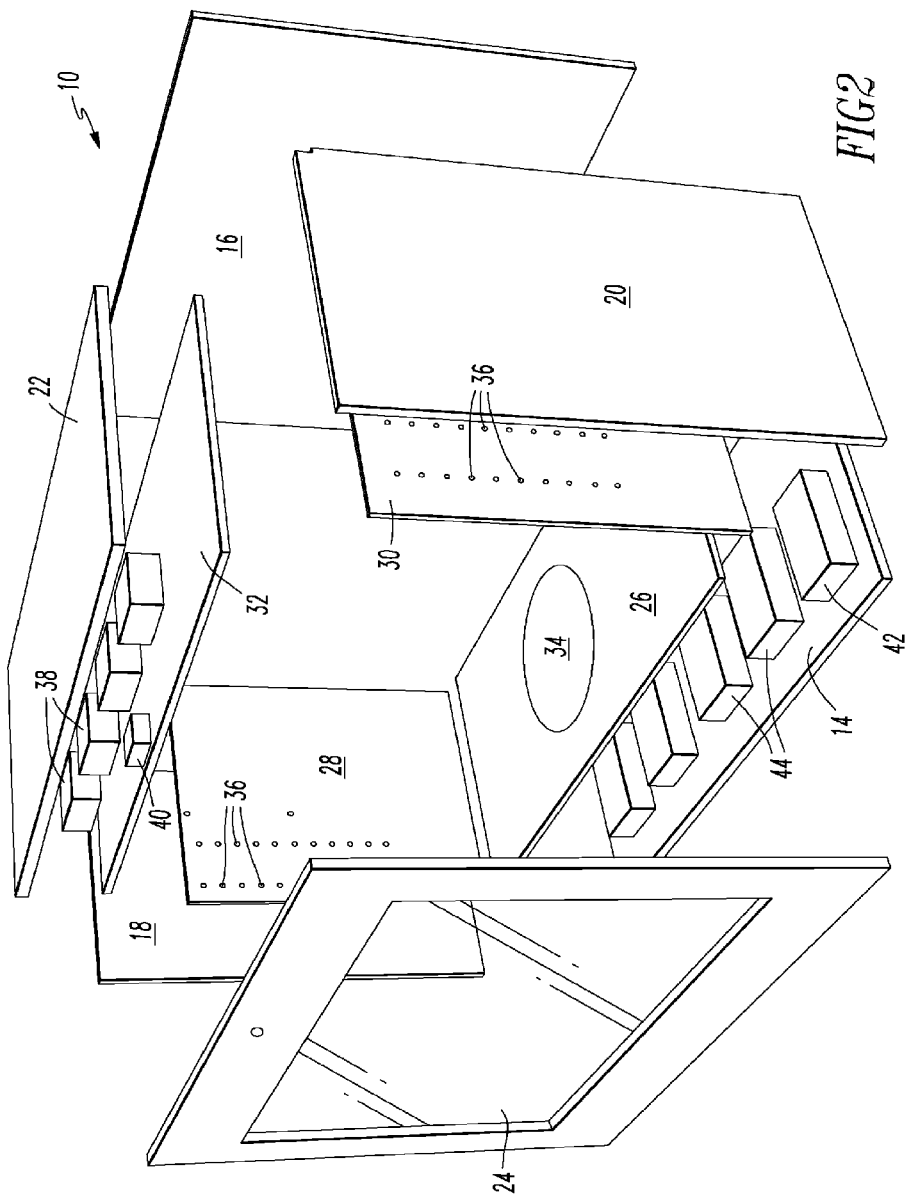

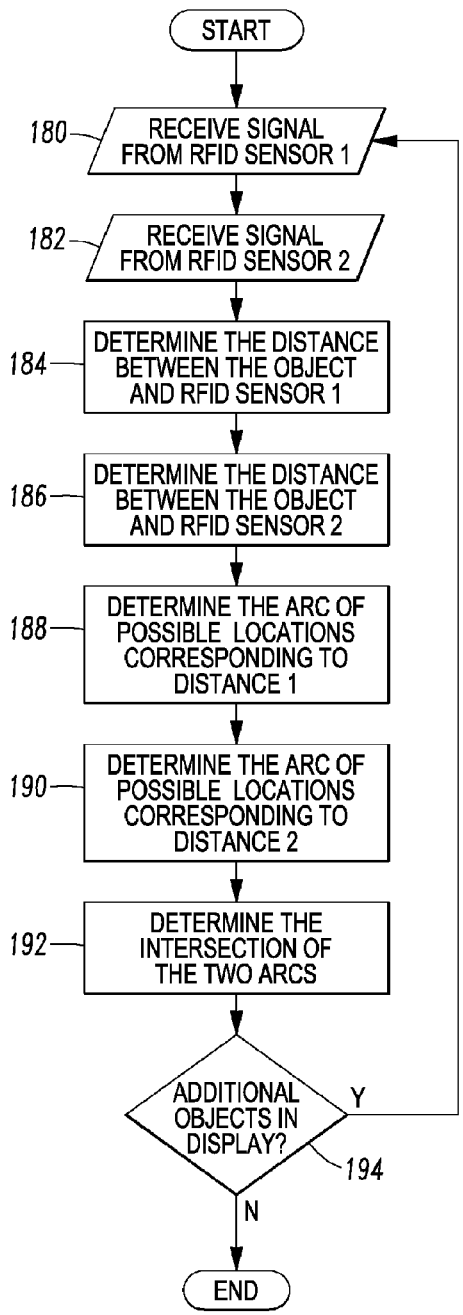
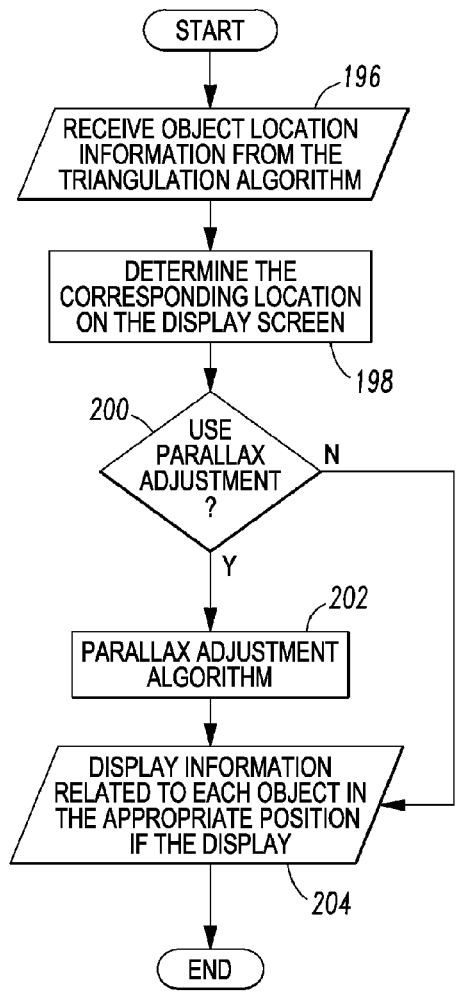
FIG.20
FIG.21

DISPLAY APPARATUS INCLUDING A TRANSPARENT ELECTRONIC MONITOR

CROSS REFERENCE TO RELATED APPLICATION

This application claims the benefit of U.S. Provisional Patent Application Ser. No. 61/722,155, which was filed on Nov. 3, 2012, and entitled "Display Apparatus Including a Transparent Electronic Monitor."

TECHNICAL FIELD

The present invention relates to devices and methods for combining a transparent electronic monitor with a physical object to provide a unique visual display.

BACKGROUND INFORMATION

Advertisers and merchants have always sought to display their products in a manner that calls the attention of consumers to the desirable features of the products. Towards this end, various combinations of informational displays and visual displays of the product have been proposed.

One example of a display device is disclosed by US 2012/0038868. The display device includes a liquid crystal display (LCD) module having a light source disposed behind the module, and a polarizing plate disposed between the light source and LCD module. The display further includes a transparent reflector that is spaced from the LCD display. The transparent reflector polarizes the image from the LCD module, with the polarization being controlled by the distance between the LCD module and reflector, as well as the angle of the reflector with respect to the LCD module. Potential uses are generally described as combining an image and a real object with an image during an exhibition, magic show, or launching show. Environments for which the screen may be useful include stages, stores, offices, vehicles, public transportation, cellular phones, and personal digital assistants, although specific uses are not discussed beyond this list. Controlling the extent to which an object behind the screen is visible by controlling the transparency of the transparent reflector is also disclosed. The transparency is controlled by controlling the luminance of the light source.

US 2008/0192027 discloses an interactive window display. Acoustic sensors located in close proximity to the four corners of the window are utilized to detect the presence of a shopper in front of a storefront window. A transparent display is located within the store so that it is visible through the storefront window. The interior of the store is visible through the transparent display. Audio information may be provided to the exterior of the store. The system is programmed to respond to taps on the window with various incentives to enter the store, based on the locations of the taps. The display screen is preferably a transparent refractive panel upon which an image can be projected from the rear at an oblique angle, and displayed clearly toward the front.

US 2011/0163986 discloses a mobile device that displays content on a dual touch screen based on a transparent display. The touch screen includes touch sensors on both sides of the display. Transparency of the display is controlled by the brightness of the displayed colors.

US 2010/0002175 discloses a method of manufacturing a transparent display screen. The method attempts to balance the capability of displaying all colors on the screen while also transmitting light through the screen. A color conversion layer may be placed in a non-chroma state in order to transmit light through the panel, or in an opaque state in which the layer appears black, and blocks transmission of light. A color display layer may display various colors when the color conversion layer is in an opaque state. The device may also transmit a color while in a transparent state.

US 2012/0120007 discloses a transparent display apparatus. The display apparatus may include a touchscreen or proximity sensor for detecting the presence of an object in proximity to the display apparatus. A timing controller, scan driver, data driver, pixel unit, subject recognition unit, and data processor are provided.

US 2011/0128386 discloses an interactive device. The device includes a pair of infrared cameras, as well as a peripheral visible light camera, for detecting objects and movements on the opposite side of a screen. The user may interact with the display that is presented by the display screen by utilizing the movements of the user's hands, fingers, or a handheld object in close proximity to the screen.

Transparent electronic monitors presently exist in the form of non-backlit liquid crystal displays (LCD) made by Samsung and LG. Unlike a backlit LCD display, non-backlit LCD displays appear black in the absence of a separate lighting source to the rear of the LCD display. When a light source is provided, the content on the screen becomes visible, and the screen becomes transparent, so that objects behind the screen become visible. Although the basic idea of incorporating a transparent LCD screen into a retail or advertising product display is known, numerous possibilities exist for enhancing such product displays. Furthermore, such non-backlit LCD screens present opportunities to create many other unique visual displays, which are not limited to advertising or retail uses.

SUMMARY

Various examples of display devices providing different combinations of features and advantages are provided. The display devices include a display case having a floor, a pair of sides, a back, and usually a ceiling. The front of the display case is formed by a nonbacklit video display, for example, a presently available nonbacklit LCD display. The absence of backlighting makes such LCD displays transparent when a light source is positioned behind the LCD display. The light source is also necessary for viewing text or other indicia displayed on the nonbacklit LCD display.

One example of the display device includes a standard, backlit video display screen forming the back panel of the display case, and potentially serving as an illumination source for the non-backlit display, illuminating desired portions of the non-backlit display, and leaving the remaining portions of the non-backlit display opaque.

Another example of the display device includes a turntable disposed within the display case, as well as by user input device, and a central processing unit operatively connected to both the turntable, the user input device, and the nonbacklit display. A viewer may control the rotation of the turntable through the input device, with indicia on the nonbacklit display being adjusted accordingly.

Another example of the display device includes a camera or sensor's structured to detect a position of a viewer, as well as a central processing unit structured to move indicia displayed on the video display in response to the position of a viewer. Some examples may correct for parallax between the viewer, indicia displayed on the display screen, and the object within the display device.

Yet another example of the display device includes one or more sensors that are structured to read indicia that is disposed on an object that is placed within the display device. The display device may thereby determine the type of object placed within the display device. Furthermore, the specific location of the object within the display device may optionally be determined.

Another example of the display device utilizes a switchable LCD film disposed on the back of the non-backlit LCD display. The switchable LCD film permits the non-backlit LCD display to selectively appear black, to appear opaque while displaying indicia, and to appear transparent while displaying indicia.

A further example of the display device includes a polarized mirror disposed in front of the nonbacklit video display.

Another example of the display device utilizes the display case as an animal habitat. Some examples of the animal habitat utilize a switchable LCD film disposed on the back of the non-backlit LCD display, permitting viewers to selectively view indicia displayed on the non-backlit LCD display, or to view animals within the animal habitat. Other examples may include sensors for tracking the position and movement of animals within the animal habitat. This information permits the central processing unit to generate interesting or entertaining indicia that can be displayed on the non-backlit LCD display, and which move across the non-backlit LCD display in a manner that tracks animal movements. Still other examples of animal habitats may include further cameras or sensors for tracking viewers, so that the position of indicia on the non-backlit display screen can be adjusted to correct for parallax between the viewer, display screen indicia, and animal.

Various methods of utilizing the different examples of display devices are provided. One example includes providing a standard, backlit video display screen behind the nonbacklit video display screen. Preselected portions of the backlit video display are illuminated, thereby illuminating corresponding portions of the nonbacklit video display. Objects disposed between the two video displays are thereby visible only through the illuminated portion of the nonbacklit video display.

Another method includes providing a camera or sensor structured to detect a position of a viewer, and a central processing unit operatively connected to the camera or sensor and to the video display screen. Indicia displayed on the video display screen is moved in response to movements of the viewer. In some examples, movements of the displayed indicia may be done in a manner that reduces parallax between the viewer, the displayed indicia, and any object within the display case.

Yet another method includes providing a sensor within the display case that is structured to read and indicia disposed on an object to be placed within the display case. The type of objects displayed within the display case may thereby be identified automatically, with the indicia displayed on the video display screen selected accordingly.

A further method includes providing a switchable LCD film disposed on the back surface of the nonbacklit video display, as well as a power supply for the switchable LCD film and a light disposed behind the nonbacklit video display. With the switchable LCD film being present, but not powered, light passing through the nonbacklit video displays will enable viewing indicia displayed on the display screen, but the display screen will be opaque. When power is applied to the switchable LCD film, then the nonbacklit video display screen becomes transparent, permitting both the indicia displayed on the screen and objects behind the screen to be viewed.

A method of displaying animals within an animal habitat is also provided. The animal habitat is formed by the display case. Some examples of the animal habitat include a switchable LCD film disposed on the back surface of the nonbacklit display screen. By selectively applying power to the switchable LCD film, indicia on the display screen or the animals within the animal habitat may be selectively displayed. Some examples may include sensors for tracking the movements of animals within the animal habitat. Indicia on the nonbacklit display screen may track the movements of these animals.

These and other aspects of the display device and method will become more apparent through the following description and drawings.

BRIEF DESCRIPTION OF THE DRAWINGS

FIG. 2 is an isometric exploded view of the display case of FIG. 1.

FIG. 20 is a flowchart showing another triangulation algorithm for use with the display case of FIG. 12.

FIG. 21 is a flowchart showing the use of the results of a triangulation algorithm to display information corresponding to objects in the display case of FIG. 12 in an appropriate location with respect to each object.

Like reference characters denote like elements throughout the drawings.

DETAILED DESCRIPTION

Figure 1A:
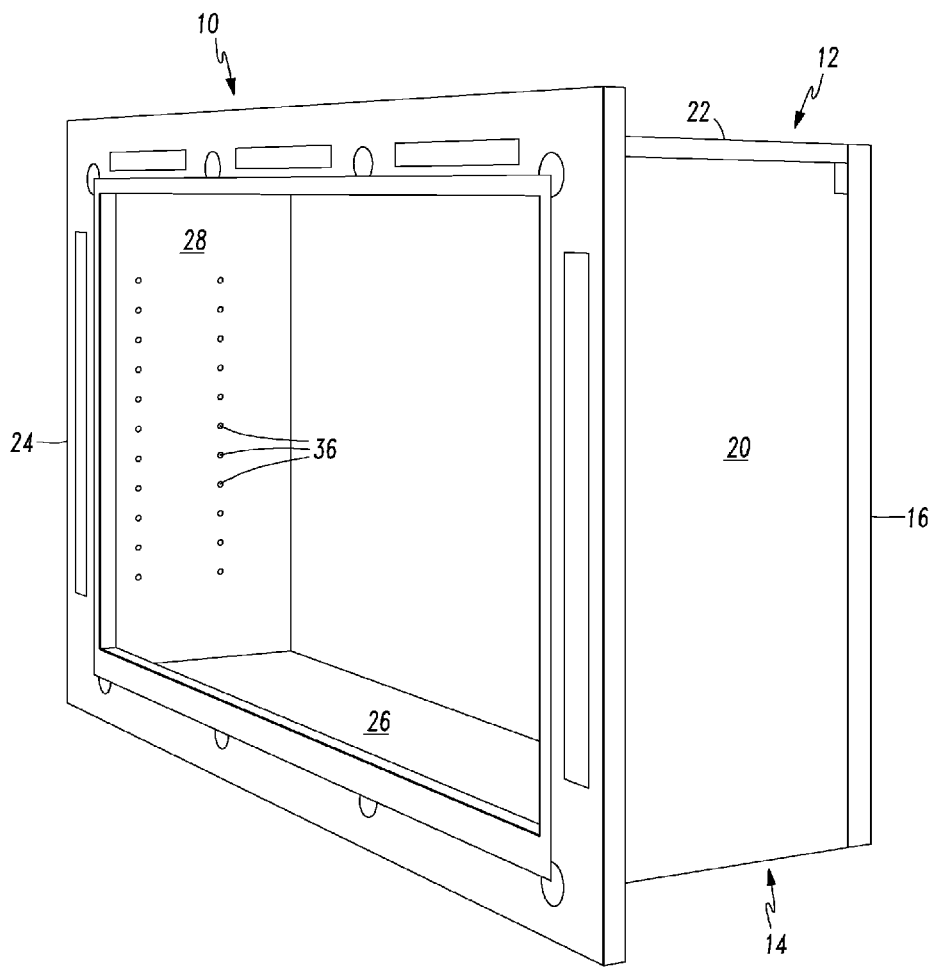
FIG. 1A is a front and side isometric view of a display case.
Figure 1B:
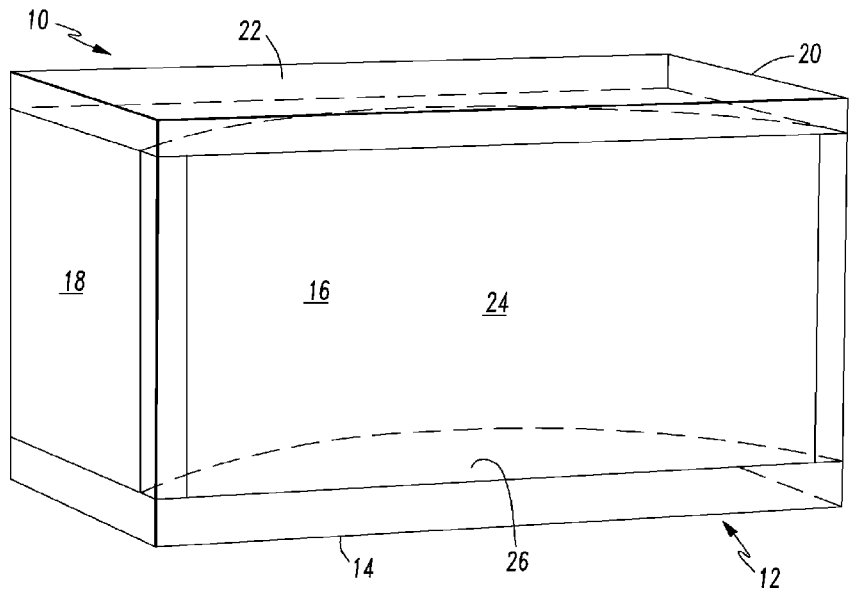
FIG. 1B is a front and side isometric view of another display case.

Referring to FIGS. 1A-2, and example of a display case 10 is illustrated. The display case 10 includes a housing 12 that includes a bottom 14, a back 16 (which may be flat as shown in FIG. 1A, or a curved diffusion panel as shown in FIG. 1B, depending on the desired interior appearance), a left side 18, a right side 20, and a top 22. In some examples, as described in greater detail below, the back 16 may be formed from a standard opaque monitor. A transparent display 24, which in the illustrated example is a transparent (nonbacklit) liquid crystal display (LCD), forms the front of the display case 10. Transparent LCD displays are presently available from both Samsung and LG. The interior of the display case 10 may be configured in a wide variety of manners, depending on the products which will be displayed, with numerous alternative configurations described below. In the example illustrated in FIG. 2, the interior of the display case 10 includes a floor 26, a left side 28, a right side 30, and a ceiling 32. In the illustrated example, the ceiling 32 is a light diffusion panel. In the illustrated example, the floor 26 includes an optional turntable 34, which is described in greater detail below. The interior left side 28 and right side 30 may include various shelf mounting structures, which in the illustrated example includes the apertures 36 defined within the left side 28 and right side 30 interior walls.

Various electronic components may be disposed in various locations between the interior housing and the exterior housing, with one illustrative example configuration being provided in FIG. 2. A plurality of LED lighting modules 38 are disposed between the ceiling 32 and top 22. One or more optional cameras or sensors 40, which may have one of a plurality of functions discussed below, may also be disposed in this location. A central processing unit (CPU) 42, which in some examples may be a solid state media player, and in other examples may be a programmable microcontroller, is disposed between the bottom 14 and floor 26. A plurality of lighting control modules 44 are also disposed between the bottom 14 and floor 26. Any of these components could optionally be placed in a different location within the housing.

Figure 3:
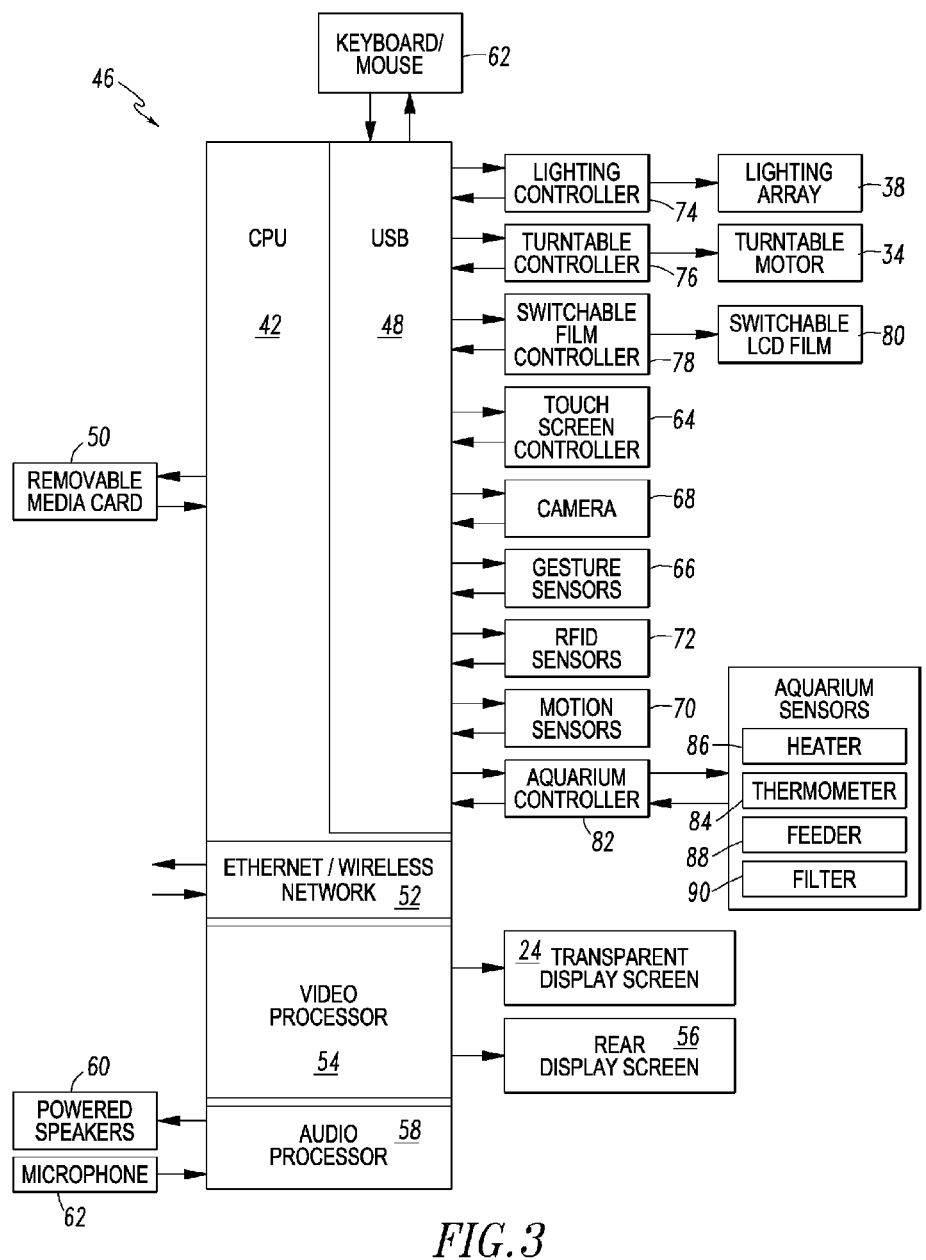
FIG. 3 is a schematic diagram showing the various components of the display case of FIG. 1.

Referring to FIG. 3, a control system 46 for the display case 10 is illustrated. The entire system is controlled by the CPU 42, which is in communication with the other system components through the bus system 48. A removable media storage device, such as the illustrated removable media card 50, or a USB drive, CD, DVD, or any other magnetic or optical storage medium, may be placed in communication with the CPU 42. The CPU 42 may also include an ethernet/wireless network 52 for receiving information or instructions from a remote location, a video processor 54 for transmitting data to the transparent display screen 24 and an optional rear display screen 56 (described below), and/or an audio processor 58 for transmitting data to one or more optional speakers 60, and/or receiving data from the optional microphone 62.

The CPU 42 may receive data and/or instructions from a variety of other sources. A standard computer input device 62, which may be a standard keyboard or mouse, may be utilized to program the CPU, or by a viewer of the display case 10 to select information to be viewed, or control other functions of the display case 10. As described in greater detail below, the transparent display 24 may optionally be a touchscreen, permitting the user of the display to enter information and/or make selections by touching predetermined locations on the transparent display 24. In this instance, a touchscreen controller 64 is provided to interpret the input received from the display 24, and transmit the data to the CPU 42. The control system 46 may further be provided with a gesture sensor 66, so that selections may be input through the use of hand gestures performed in front of the gesture sensor 66. A camera 68 and/or motion sensor 70 may be utilized to detect the presence and/or movements of a viewer, providing this information to the CPU 42 for purposes that will be described below. One example of a suitable cameras and gesture sensor system is the Kinect for Windows sensor available from Microsoft. Another example is disclosed in US 2011/0128386, the entire disclosure of which is hereby incorporated by reference.

Radiofrequency identification (RFID) sensors 72 may be provided to provide automatic identification of items placed within the display case 10. Some examples of the display 10 may utilize multiple RFID sensors 72, as explained below. In the case of multiple RFID sensors 72, the signal from each sensor will be read separately to facilitate determining the location of one or more items within the display 10 through triangulation, as explained in greater detail below.

The CPU 42 provides a variety of control systems for the various components of the display case 10. A lighting controller 74 is utilized to control the lighting modules 38, and in some examples will utilize DMX signals to control the lighting modules 38. A turntable controller 76 is utilized to start, stop, and select to the direction of rotation of the turntable 34. A switchable film controller 78 is utilized to control an optional switchable LCD film 80 in a manner that is described in greater detail below. Lastly, if the interior of the display 10 is utilized as an aquarium or other animal habitat as described in greater detail below, an aquarium controller 82 may receive information from a thermometer 84 as well as other optional aquarium sensors, and will provide control signals to an optional heater 86, a feeder 88, and a filtration system 90.

Figure 4:
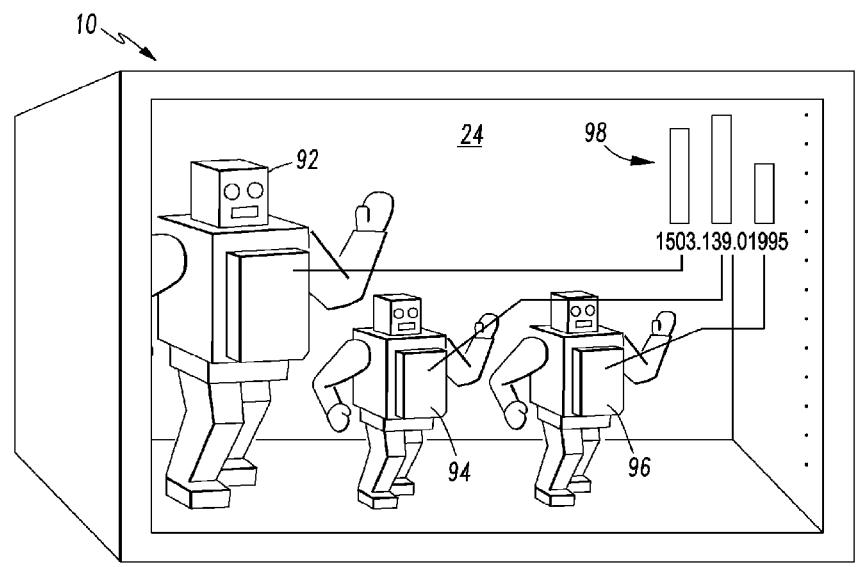
FIG. 4 is an isometric front and side view of the display case of FIG. 1.

A basic implementation of the display case 10 is illustrated in FIG. 4. A plurality of children's toys 92, 94, 96 have been placed in the display case 10. Information 98 about the toys 92, 94, 96 is displayed on the display screen 24. When the lighting modules 38 are lit, the toys 92, 94, 96 are visible through the display screen 24. A consumer viewing the display 10 will therefore be able to view the products 92, 94, 96 as well as the information 98 by viewing the screen 24.

Figure 5:
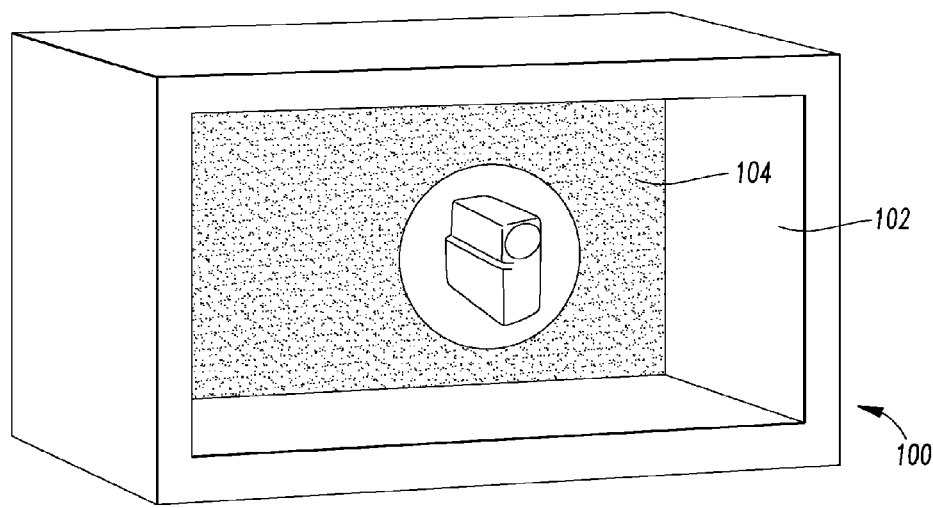
FIG. 5 is an isometric front and side view of an alternative example of a display case.
Figure 6:
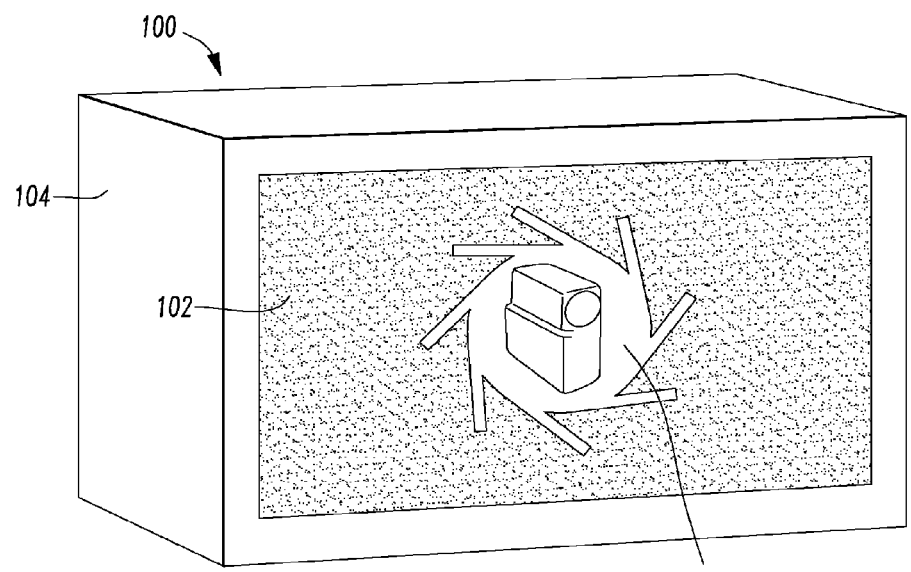
FIG. 6 is an isometric front and side view of the display case of FIG. 5.

One alternative example of a display case 100 is illustrated in FIGS. 5-6. The display case 100 includes two LCD displays, one of which being the front transparent LCD display 102, and the second being a standard opaque monitor 104 forming the back panel of the display. Advertising and/or informational displays may be coordinated between the transparent display 102 and the opaque display 104. Animated type, motion graphics, slideshows, and video clips may be choreographed to interplay with the product and the display screens 102, 104. As one example, text callouts and animated elements could appear to jump back and forth between the screens 102, 104. Alternatively, the opaque monitor 104 can be utilized to provide localized lighting for the transparent display 102. In the absence of backlighting, the transparent display 102 will appear to be black. As shown in FIG. 6, a highlight elements on the display 104 can be utilized in conjunction with the lighting modules 38 to provide a localized viewing aperture 106 by effectively backlighting only the portion of the display 102 corresponding to the aperture 106. The remaining, unbacklit sections of the transparent display 102 will appear black.

Figure 7:
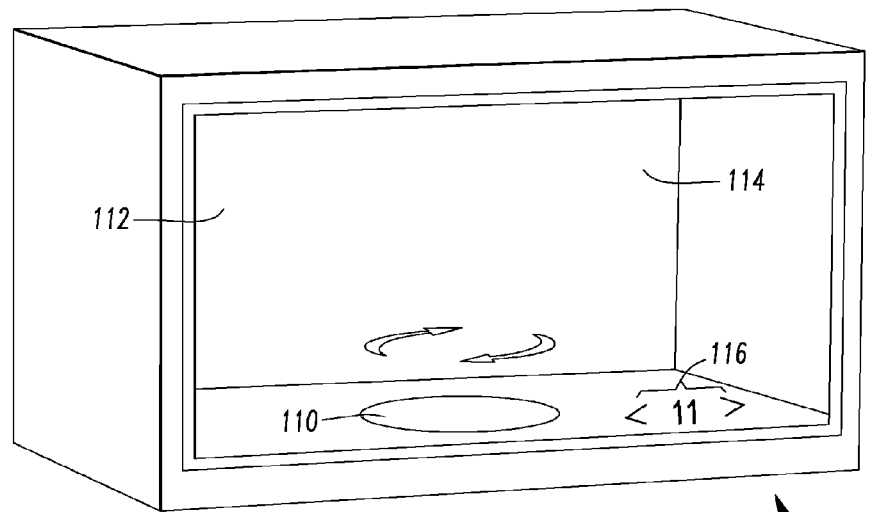
FIG. 7 is an isometric front and side view of another alternative example of a display case.
Figure 8:
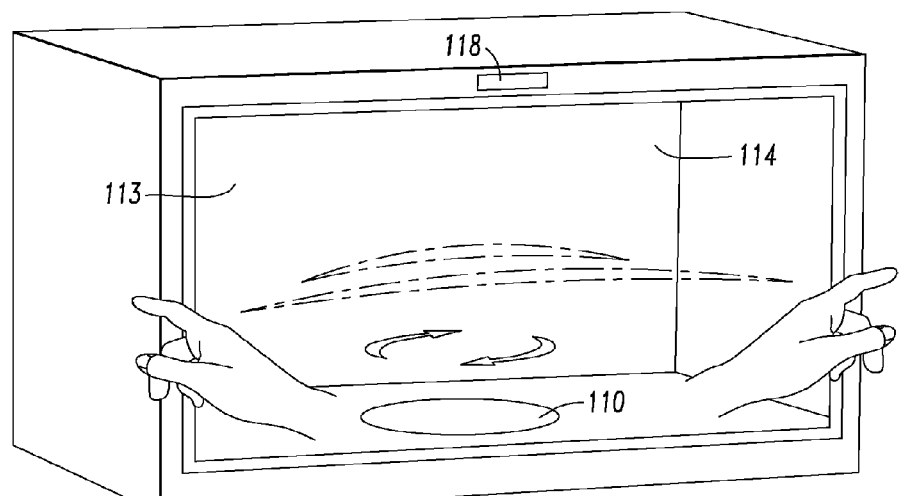
FIG. 8 is an isometric front and side view of the display case of FIG. 7.

Further examples of a display case 108, 109 are illustrated in FIGS. 7-8. The display cases 108, 109 include a turntable 110 for rotating an item within the display case 108, 109. The display cases 108, 109 include a transparent display 112, 113. The back panel 114 of the display cases 108, 109 may optionally be a standard opaque monitor as described above. Information displayed on the transparent display 112, 113 and optional back panel monitor 114 may be coordinated with the rotation of the turntable 110. For example, information about features of the items that are currently visible to a viewer may be displayed on a transparent display 112, with the information changing as the turntable 110 rotates to show different features of the displayed item. As another alternative, features that are located in rearward portions of the displayed item may be displayed on an opaque monitor as described above forming the back panel 114, switching to the transparent display 112, 113 as the turntable 110 rotates to bring these features of the item towards the front of the display cases 108, 109.

In some examples of the display case 108, rotation of the turntable 110 may be controlled by the viewer utilizing a variety of control mechanisms such as a keyboard mouse, touch pad, etc. One example of such a control mechanism is included within the display case 108. The transparent display 112 is a touchscreen display that is illustrated with indicia 116 displayed thereon. A viewer may cause the turntable 110 to rotate in a desired direction by touching the arrow corresponding to that direction. In the example of display case 109, an integrated camera and gesture sensor 118 are utilized to track the hand motions of a viewer. Suitable gesture sensing devices include the Kinect for Windows sensor as well as the device disclosed in US 2011/0128386. The viewer may cause the turntable 110 to rotate in a desired direction, or to pause, by moving their hand in the desired direction of rotation. The camera and gesture sensor 118 could be utilized for other purposes as well. For example, vertical hand movements could be utilized to brighten or dim the lighting modules 38, to scroll information displayed on the transparent display 113, to select options displayed on the transparent display 113, and/or to navigate various content layers shown on the transparent display 113.

Figure 9:
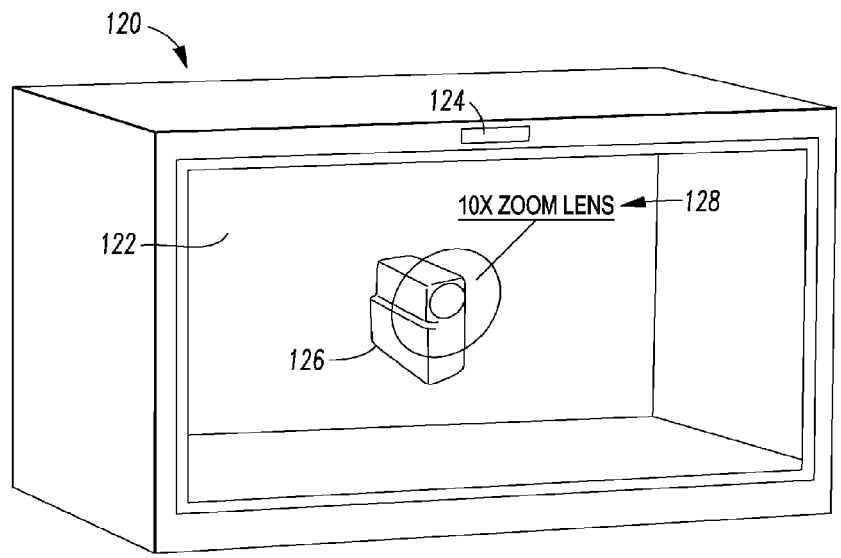
FIG. 9 is an isometric front and side view of a further alternative example of a display case.
Figure 10:
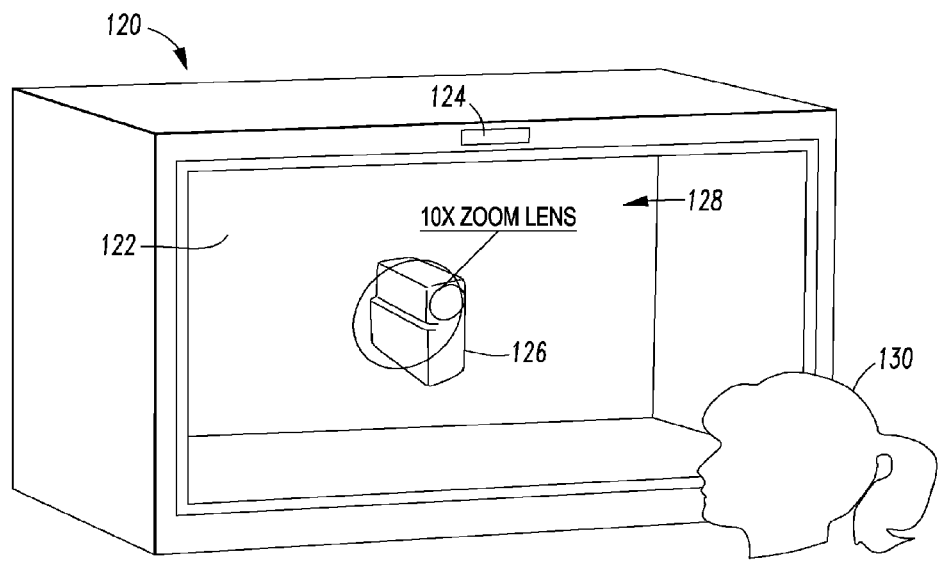
FIG. 10 is an isometric front and side view of the display case of FIG. 9.
Figure 11:
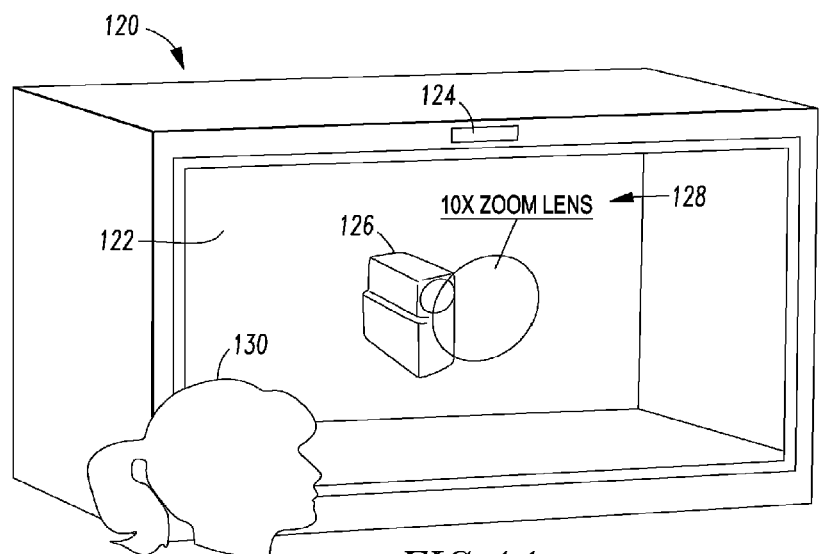
FIG. 11 is an isometric front and side view of yet another alternative example of a display case.

Referring to FIGS. 9-11, another example of a display case 120 is illustrated. The display case 120 includes a transparent LCD screen 122, as well as a depth sensing camera 124. By determining the distance between the camera and objects seen by the camera, the camera can determine the position of a viewer's face, which would obviously be relatively close relative to other objects in the environment. FIG. 9 illustrates an example of a video camera 126 within the display case 120, with a feature of the video camera shown on the transparent display screen 122. When a customer is directly in front of the display case 120, the relative appearance of the camera 126 and indicia 128 displayed on the screen 122 is shown in FIG. 9. FIGS. 10 and 11 illustrate the parallax resulting if the customer 130 is located closer to the right side (FIG. 10) or left side (FIG. 11) of the display case 120. In the absence of any adjustments to the indicia 128 displayed on the transparent screen 122, this parallax will cause the presentation of the indicia 128 with respect to the camera 126 to be skewed. By utilizing the depth sensing camera 124 to detect the position of the customer 130, the indicia 128 may be moved to a different location on the display screen 122 as appropriate so that regardless of the position of the customer 130, the image viewed by the customer 130 will appear as it does in FIG. 9.

The CPU of the display case 120 may be programmed with a threshold proximity value so that, if a single viewer is viewing the display case 120 while others travel past the display case 120, those travelling in the background are ignored unless they come within a predetermined distance of the display screen 122, and also slow their walking to a predetermined speed and/or remain within the threshold distance for a predetermined period of time, as would occur if they began to view the display screen 122. This allows the parallax correction algorithm to focus only on a viewer or viewers who are actually engaged in viewing the display screen 122.

Figure 22:
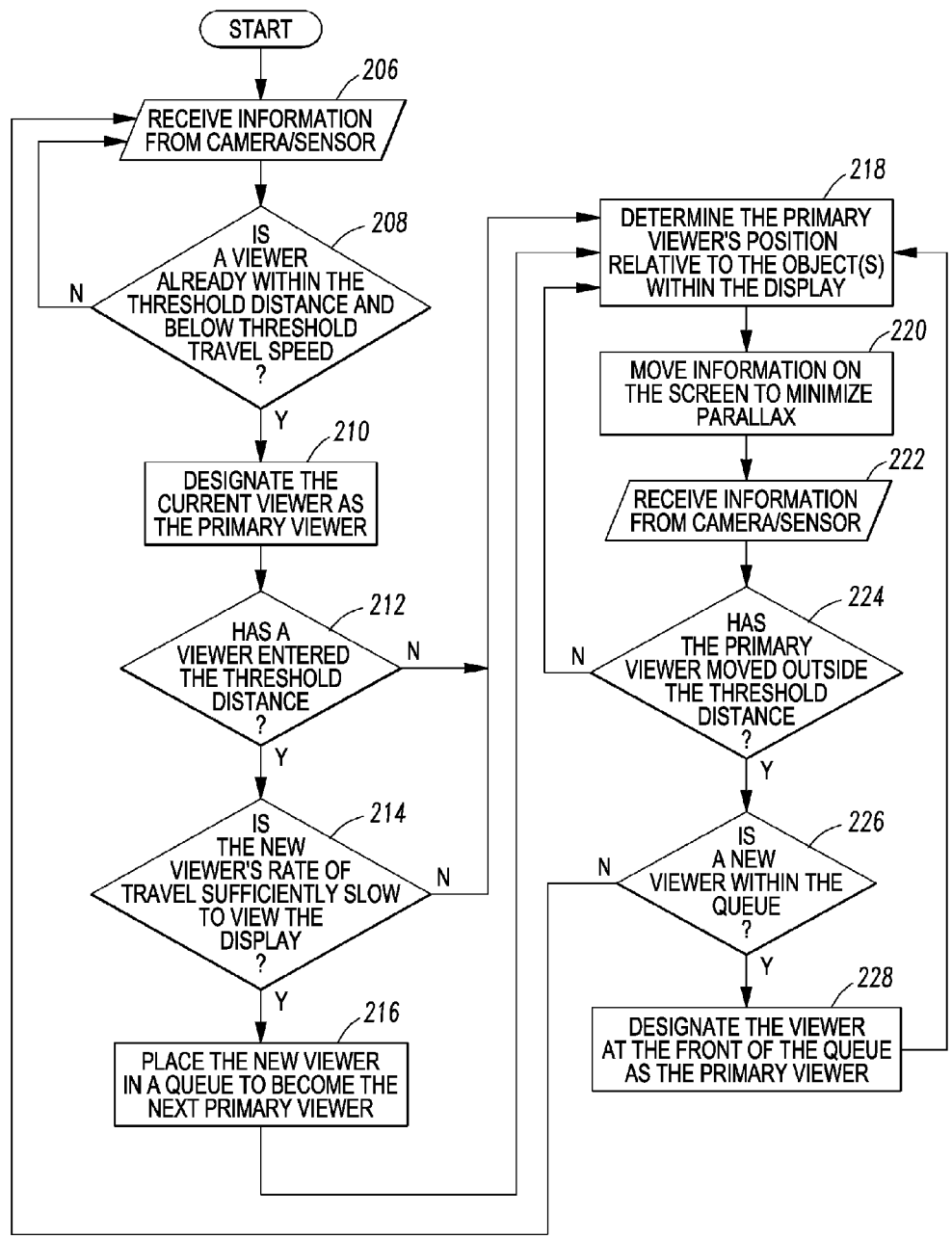
FIG. 22 is a flowchart showing one parallax correction algorithm.

If multiple viewers are present, then the system may take this into account in a few different ways. As one option, the system could focus on correcting parallax for a primary viewer, ignoring the other viewers. Referring to FIG. 22, the system receives information from a camera 124 at step 206. Next, it is determined whether a viewer is within the threshold distance, and whether the viewer has slowed or stopped to view the display, at step 208. If no viewer is within the threshold, the system continues to monitor the threshold area at step 206 until a viewer enters the threshold area. When a viewer is present, the first viewer to enter the threshold area is designated as the primary viewer at step 210. If another viewer enters the threshold distance as determined at step 212, and if that viewer slows their rate of travel sufficiently to indicate that they may be viewing the display as determined at step 214, then that viewer is placed in a queue at step 216 to become the next primary viewer if the current primary viewer leaves.

Once the primary viewer has been identified, the viewer's position is determined with respect to objects within the display at step 218. For this purpose, it may be assumed in some cases that the object is in a predetermined location within the display case. Alternatively, if RFID sensors or other sensors (described below) are utilized, the location of the object within the display case as determined by these sensors is utilized. With the location of the primary viewer and the objects in the display case known, appropriate geometric calculations can be made to move information on the display screen 122 to a different location on the display screen 122 to correct for parallax at step 220. Information from the camera 124 is again received at step 222. If the primary viewer is still present as determined at step 224, the system returns to step 218 and continues to track the movements of the primary viewer. Otherwise, if the primary viewer has left, the system next checks at step 226 to determine whether there is another viewer within the queue. If so, then the first viewer in the queue is designated as the primary viewer at step 228, and the system determines the new primary viewer position at step 218. Otherwise, the system returns to step 206 to begin scanning for other viewers to enter the threshold criteria.

Figure 23:
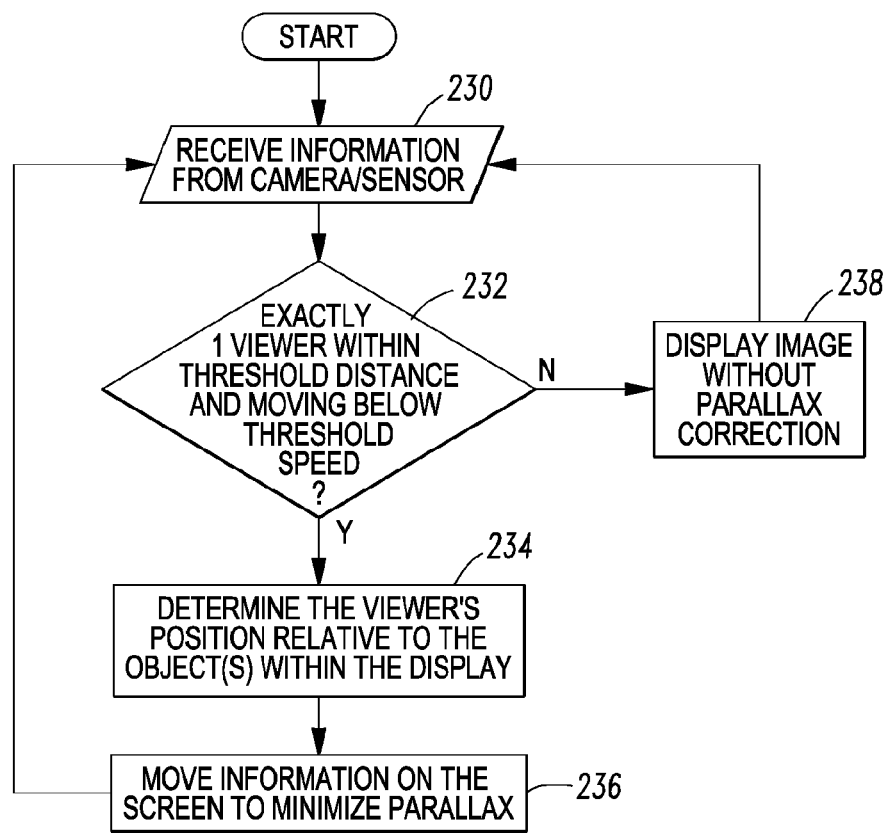
FIG. 23 is a flowchart showing another parallax correction algorithm.

As another option, the system could recognize that reducing parallax for one viewer will create worse parallax for another viewer, and thereby avoid adjusting for parallax unless the number of viewers inside the threshold distance is limited to one. Referring to FIG. 23, the system first receives information from camera 124 at step 230. If exactly one viewer meets the threshold criteria for proximity and speed of travel at step 232, then the viewer's position is determined relative to objects within the display at step 234. The appropriate geometric calculations are performed, and information on the display screen 122 is moved to the appropriate location to minimize parallax at step 236. The system then continues to receive information from the camera 124 at step 230. If there are no viewers present, or if there is more than one viewer present, information will be displayed without parallax correction at step 238.

Figure 24:
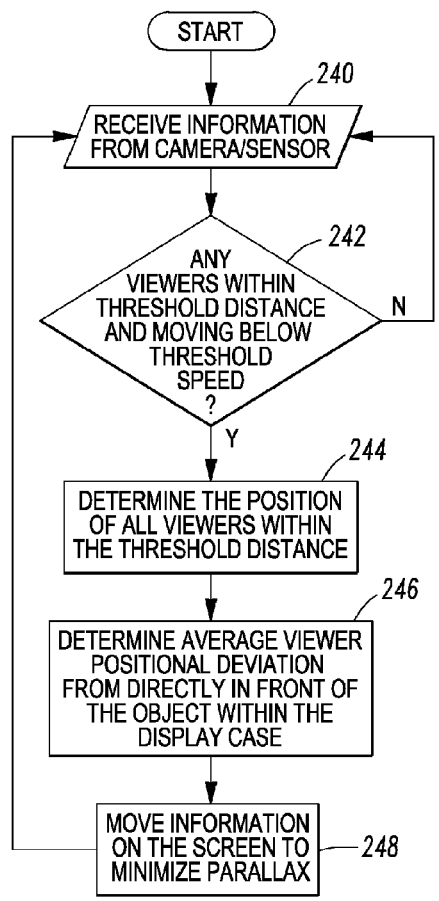
FIG. 24 is a flowchart showing yet another parallax correction algorithm.

Alternatively, if all, or a majority, of the viewers are located on one side of the screen, the system could make adjustments based on an average viewer location. Referring to FIG. 24, information is received from the camera 124 at step 240. If any viewers meet the threshold distance and speed of travel criteria at step 242, then the position of all viewers within the threshold criteria is determined at step 244. Next, the average viewer positional deviation from directly in front of the object within the display case is determined at step 246. The appropriate geometric calculations are performed based on this information, and the image on the display screen moved appropriately, at step 248. The system then continues to receive information from the camera 124 at step 240, repeating the cycle whenever viewers are present, and returning to step 240 to continue checking for the presence of viewers any time no viewers meet the threshold criteria.

Figure 12:
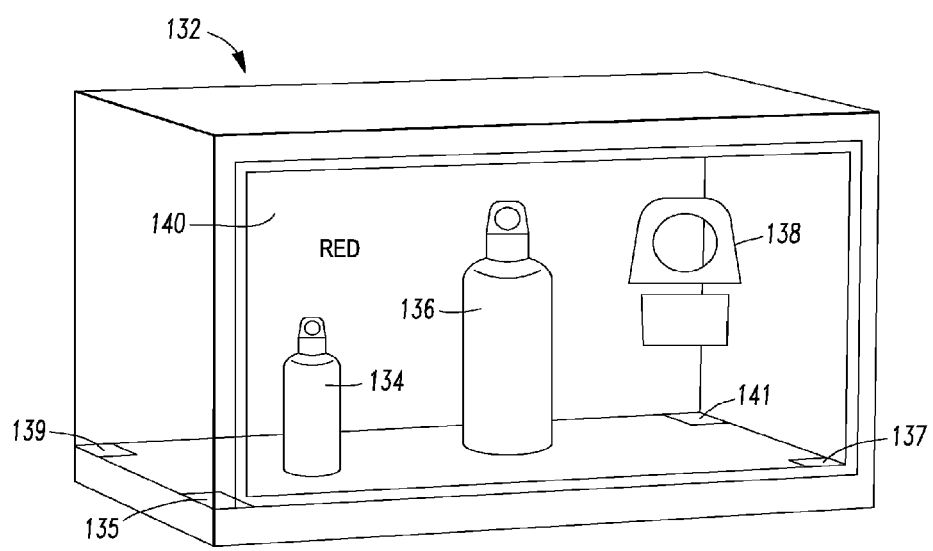
FIG. 12 is an isometric front and side view of the display case of FIG. 11.

Referring to FIG. 12, the display case 132 is illustrated. The display case 132 includes one or more RFID sensors, with sensors 135, 137, 139, and 141 being shown in each corner of the display case 132. When a product equipped with an RFID tag is placed within the display case 132, the RFID sensor can read the RFID tag to determine the products which has been placed in the display case 132. If multiple RFID sensors are utilized, then the location of multiple products within the display case 132 can be determined by comparing the relative signal strength of each RFID tag with respect to each RFID sensor (triangulation). Information about each of the products 134, 136, 138 can therefore be displayed in the appropriate location on the display screen 140.

Figure 19:
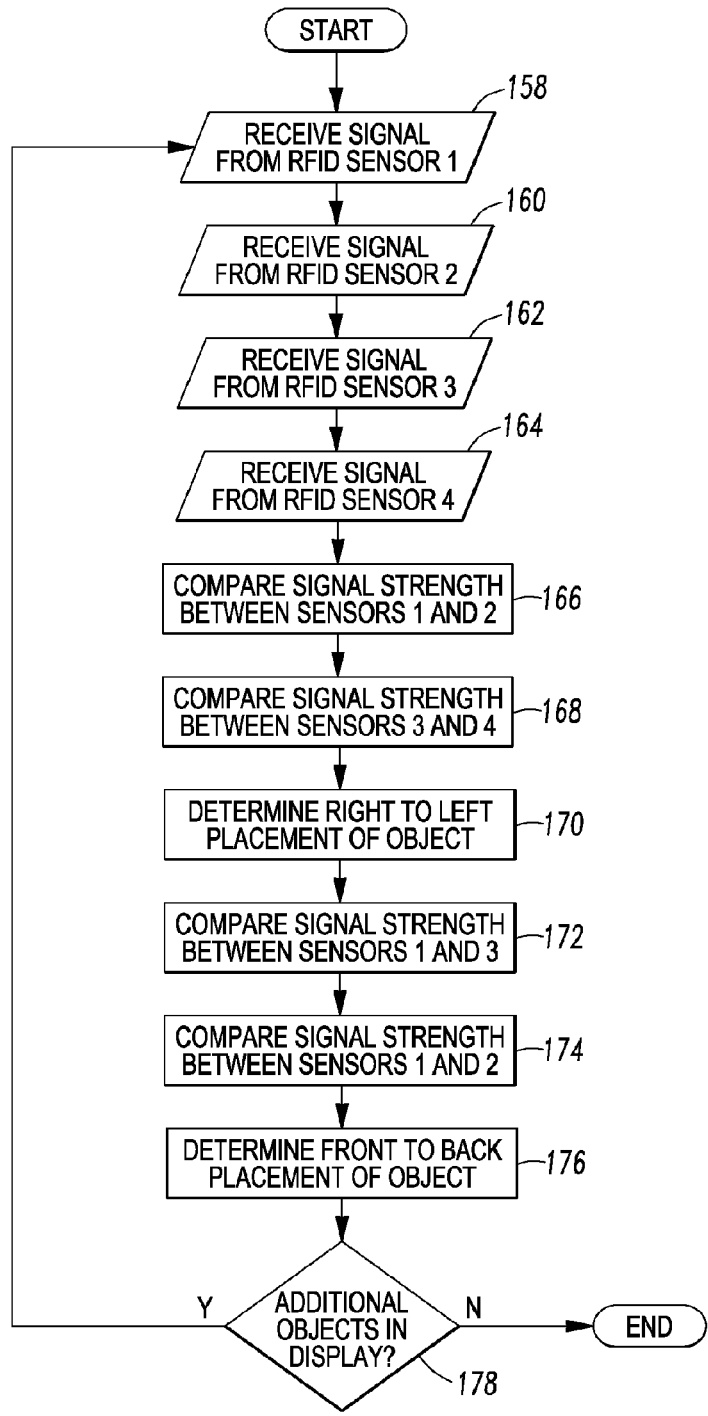
FIG. 19 is a flowchart showing a triangulation algorithm for use with the display case of FIG. 12.

Referring to FIG. 19, one alternative triangulation algorithm is illustrated. The process begins by receiving a signal from RFID sensors 135, 137, 139, 141 at steps 158, 160, 162, and 164, respectively. Next, the strength of the signals received by the RFID sensors 135, 137 is compared at step 166. Similarly, the signal strength of the signals received by the RFID sensors 139, 141 is compared at step 168. The relative signal strengths between the values read at each sensor is utilized to determine the left to right placement of the object at step 170. Similarly, the signal strength received by sensors 135, 139 is compared at step 172, and the signal strength received by the RFID sensors 137, 141 is compared at step 174. These values are used to determine the front to back placement of the object at step 176. With one object within the display case 132 having been located, the process may be repeated as often as necessary for other objects within the display case 132 at step 178.

Referring to FIG. 20, an alternative triangulation method is illustrated. The method of FIG. 20 may be utilized when only two RFID sensors are present, with the RFID sensors typically being located at opposite ends of the display case 132. If we assume that sensors 139, 141 are the only two sensors present, then the signal from sensor 139 is received at step 180. The signal from sensor 141 is received at step 182. The strength of the signal received by the sensor 139 is measured, and utilized to determine the distance between the object and the RFID sensor 139 at step 184. Similarly, the strength of the signal received at the RFID sensor 141 is measured, and utilized to determine the distance between the object and the sensor 141 at step 186. Obviously, a known distance from either sensor will place the objects somewhere within a circle of that radius around the sensor. This radius is calculated for sensor 139 at step 188, and for sensor 141 at step 190. Since it is known that the object is within the display case 132, the location within the display case 132 where the two circles intersect is determined at step 192, at which point the location of the object is known. The process can be repeated for additional objects within the display case 132 at step 194.

Once the location of all objects within the display case 132 is known, this information can be utilized to display information corresponding to each object on the display screen 140. Referring to FIG. 21, information about the location of each object within the display case 132 is received at step 196. The corresponding location on the display screen is determined at step 198. If parallax adjustment as described above is being utilized (determined at step 200), then the parallax adjustment algorithm can be run at step 202. Regardless of whether parallax adjustment is used, information is displayed at the appropriate position on the display screen 140 at step 204.

Figure 13:
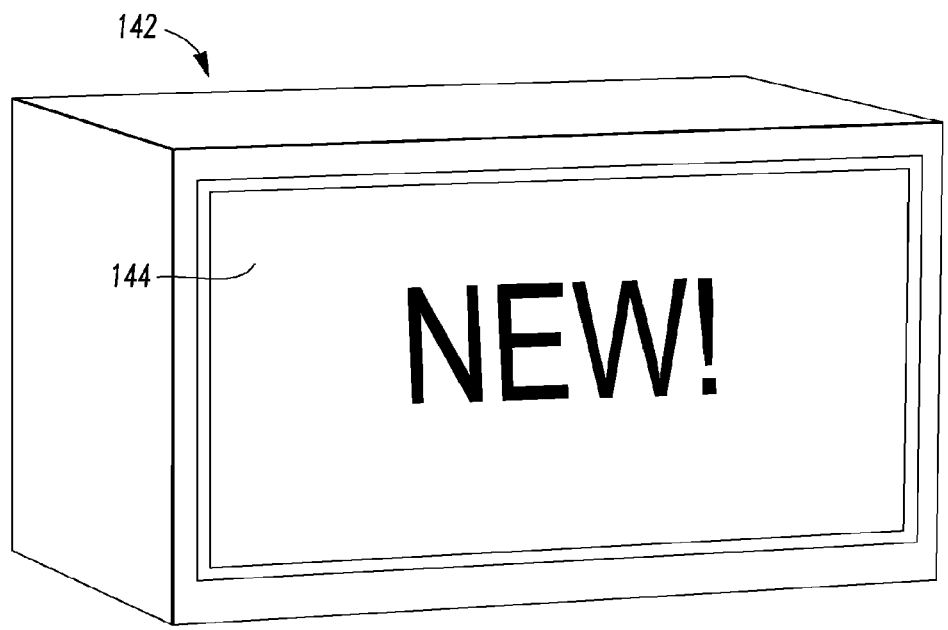
FIG. 13 is an isometric front and side view of an alternative example of a display case.
Figure 14:
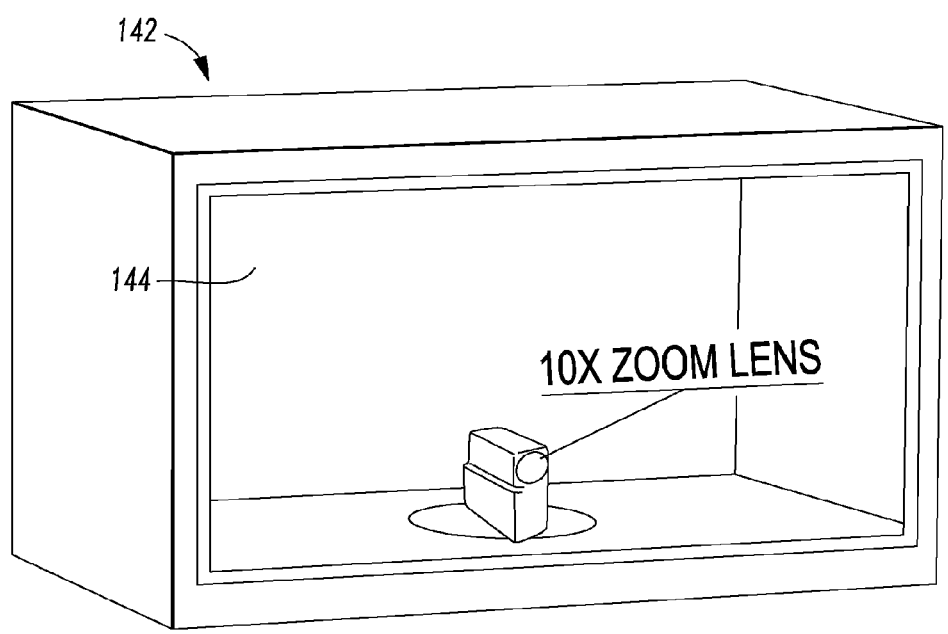
FIG. 14 is an isometric front and side view of the display case of FIG. 13.

Referring to FIGS. 13-14, a display case 142 is illustrated. The display case 142 includes a transparent display screen 144 having a switchable LCD film disposed behind the display screen 144. The LCD film may be applied to the back surface of the display screen 144, with a glass plate disposed over the LCD film. Alternatively, the switchable LCD film may be disposed between a pair of glass plates which are disposed behind the display screen 144. Suitable switchable LCD films are available from Glass Apps, LLC. Because the transparent display screen 144 is not backlit, in the absence of the switchable LCD film, it would appear black when there is no light emitted inside the display case 142. The CPU of the display case 142 is structured to selectively apply power to the switchable LCD film as shown in FIG. 3. Referring back to FIGS. 13-14, the switchable LCD film appears frosted when there is no power applied to the LCD film. In this state, the LCD film acts as a diffusion element for the LCD lights, permitting information to be displayed on the display screen 144 without revealing the contents of the display case 142, as shown in FIG. 13. When power is applied to the switchable LCD film, the switchable LCD film becomes transparent, revealing the contents of the display case 142 as shown in FIG. 14. The power applied to the switchable LCD film can be coordinated with the content displayed on the transparent display screen 144, correlating the media content with timed revealing and concealing of the contents of the display case 142.

Figure 15:
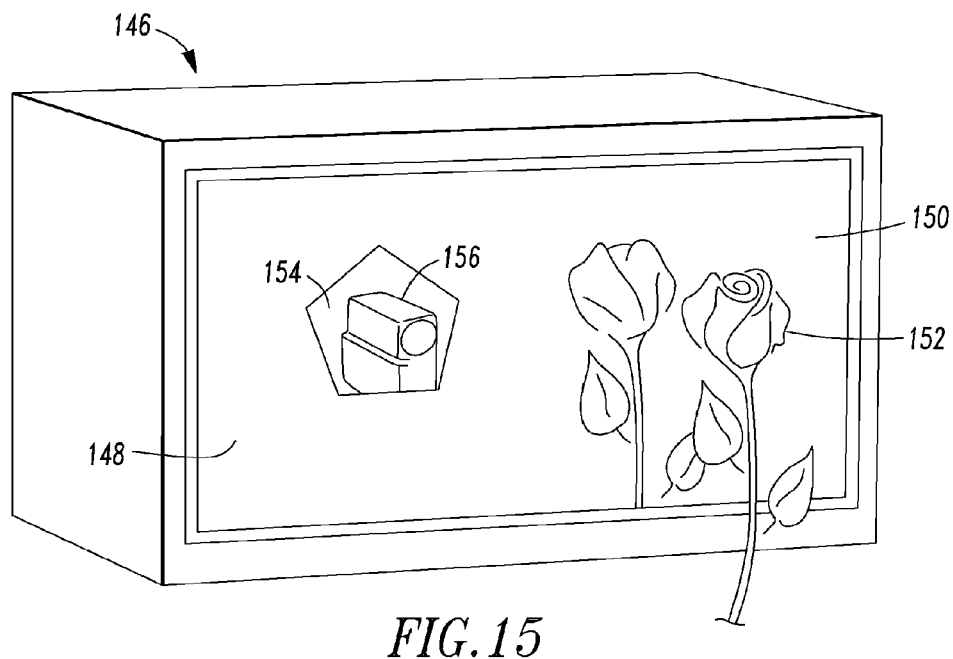
FIG. 15 is an isometric front and side view of a further example of a display case.

Referring to FIG. 15, a display case 146 includes a transparent display screen 148 over which a polarized mirror glass has been applied. The mirror coating in some examples is vapor deposited onto glass, which is then placed in front of the display screen 148. The mirror glass is carefully polarized to allow a bright image to transfer through the mirror. When the interior of the display case 146 is not lit, the display screen 148 appears as a mirror. When the display case 146 is fully illuminated, the interior of the display case 146 is visible. If the display screen 148 is utilized to display a black and white image, the black portions of the image are opaque, and the white portions appear transparent (assuming that the interior of the display case 146 is illuminated). With the inclusion of the polarized mirror glass, the black portions 150 of the image appear to be mirrored, and are shown in FIG. 15 reflecting the image of the rose 152. The white portions 154 of the image appear transparent, displaying a product 156 within the display case 146.

Figure 16:
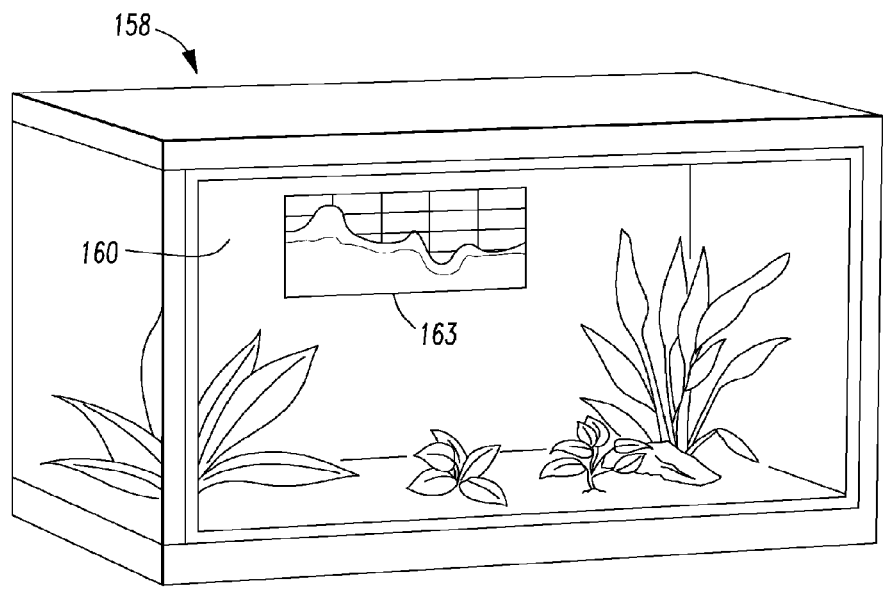
FIG. 16 is an isometric front and side view of another example of a display case.
Figure 17:
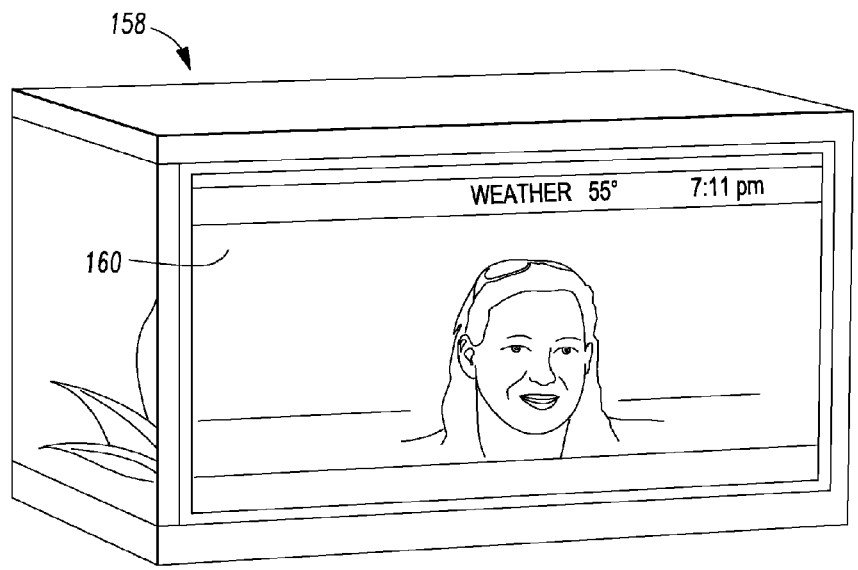
FIG. 17 is an isometric front and side view of the display case of FIG. 16.
Figure 18:
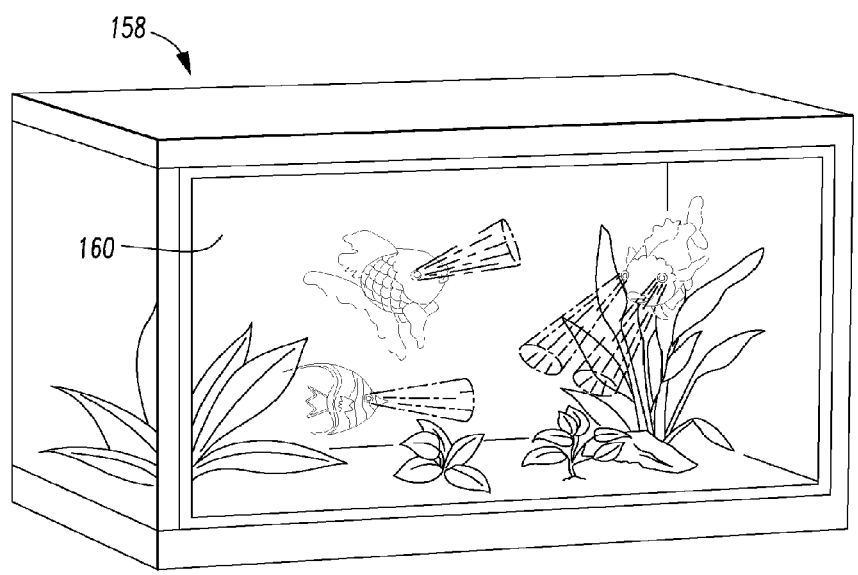
FIG. 18 is an isometric front and side view of the display case of FIG. 16.

Referring to FIGS. 16-18, an animal habitat 158, for example, the illustrated fish tank, incorporating a transparent display screen 160 is illustrated. As used herein, "animal" may refer to any mammal, fish, bird, insect, etc. that could be kept in an enclosure. Similarly, "animal habitat" may refer to a cage, glass enclosure, etc., that may contain an animal, including an aquarium for containing fish. In the example of a fish tank, the transparent display screen 160 is adjacent to one of the glass panels of the fish tank 158, allowing viewing of the fish through the transparent display screen 160, while isolating the transparent display screen 160 from the water in the fish tank 158. If a different animal habitat is used, for example, a hamster or gerbil enclosure, a glass barrier between the animals and display screen 160 may still be desirable. Some examples of the display screen 160 include a switchable LCD film, as described above, permitting either viewing of the fish within the fish tank 158 through a transparent screen 160, or the use of the screen 160 as an information display, computer monitor, television, etc. with a view of the fish being totally obscured. Some examples of the display screen 160 may include sensors for monitoring conditions such as temperature within the fish tank 158 or other animal enclosure, and displaying these conditions on the screen as shown by indicia 163. A heater, feeder, and/or filtration system may be controlled by the CPU of the screen 160, displaying information about these devices within the indicia 163.

Some examples of the animal habitat 158 include motion sensing cameras or sensors to track the movement of fish or other creatures within the animal habitat 158. Suitable fish/animal tracking devices include the Kinect for Windows sensor as well as the device disclosed in US 2011/0128386. Graphics on the display screen 160 may be integrated with the motion of the fish or other creatures. For example, headlights 161 may be displayed on the screen 160 in front of fish swimming in a fish tank 158 at night, providing for interesting visual effects. Furthermore, the parallax correction algorithm can be used to correct for parallax, so that a viewer seeing the fish from a different angle will still view the headlight graphics in appropriate locations with respect to the fish.

Figure 25:
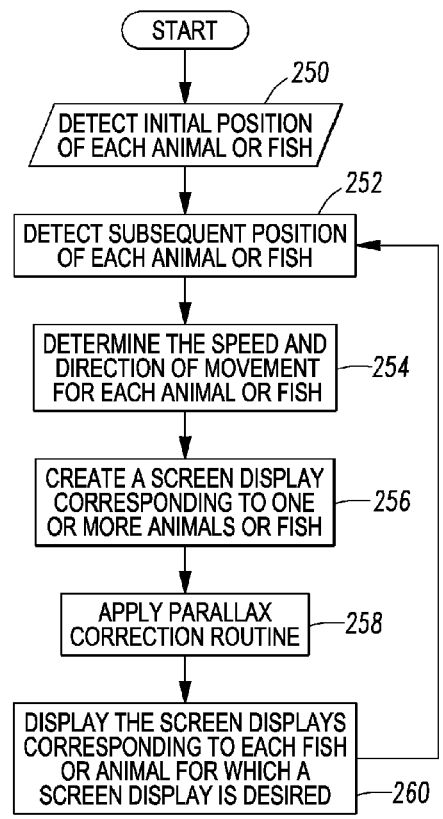
FIG. 25 is a flowchart showing the display of animated graphics on a display used in conjunction with an animal habitat.

Referring to FIG. 25, the initial position of each animal or fish is detected at step 250. A subsequent position of each animal or fish is next detected at step 252, and this information is utilized to determine the speed and direction of movement for each animal or fish at step 254. A screen display corresponding to one or more animals or fish is created at step 256. Parallax correction as described above may optionally be applied at step 258. The graphics are then displayed on the display screen 160 at step 260. The system continues to calculate subsequent positions for each animal at step 252, repeatedly using the changes in position of each fish or animals determine speed and direction of movement so that the graphics may be displayed on the appropriate location on the display screen 160.

The CPU of the transparent display screen 160 may be used to control any heaters, filtration systems, feeding systems, or other devices that may be utilized in the care of the fish or other animals within the animal habitat 158. Information such as the temperature, amount of food available, feeding times, condition of a filter, etc. can be displayed on the screen 160 as shown by display 163. If the screen 160 is a touch screen as described above, then changes to these functions can be made by touching the appropriate indicia on the screen.

A variety of modifications to the above-described embodiments will be apparent to those skilled in the art from this disclosure. For example, many of the features of the above-described examples of the display case can be combined with other features of other examples. Thus, the invention may be embodied in other specific forms without departing from the spirit or essential attributes thereof. The particular embodiments disclosed are meant to be illustrative only and not limiting as to the scope of the invention. The appended claims, rather than to the foregoing specification, should be referenced to indicate the scope of the invention.

What is claimed is:
1. An animal habitat, comprising:
   an enclosure having a floor, a pair of sides, a back, and a substantially transparent front;
   a non-backlit video display screen disposed at the front of the display case;
   a switchable LCD film disposed on a back surface of the non-backlit video display;
   means for selectively supplying power to the switchable LCD film;
   a central processing unit operatively connected to the non-backlit video display;
   at least one peripheral device that is structured to provide care for animals within the animal habitat, the at least one peripheral device being operatively connected to the central processing unit; and
   means for interacting with the non-backlit video display screen or the central processing unit to control the at least one peripheral device.
2. The animal habitat according to claim 1, further comprising means for displaying status information for the peripheral device on the non-backlit video display.
3. The animal habitat according to claim 1, wherein the means for interacting with the non-backlit video display screen are selected from the group consisting of the non-backlit video display being a touch screen, a gesture sensor operatively connected to the central processing unit, a keyboard, a mouse, and a touch pad.
4. The animal habitat according to claim 1, wherein the at least one peripheral device is selected from the group consisting of a heating system, a feeding system, and a filtering system.
5. An animal habitat, comprising:
   an enclosure having a floor, a pair of sides, a back, and a substantially transparent front;
   a non-backlit video display screen disposed at the front of the display case;
   a sensor structured to track movements of aminals within the enclosure;
   a central processing unit that is structured to cause the non-backlit video display to display indicia that changes in response to the movements of animals within the enclosure.
6. The animal habitat according to claim 5, wherein the indicia displayed on the non-backlit video display moves in response to the movements of animals within the enclosure.
7. The animal habitat according to claim 6, wherein movement of the indicia displayed on the non-backlit video display tracks movement of animals within the animal habitat.
8. The animal habitat according to claim 6, further comprising:
   a camera or sensor structured to detect a position of a viewer; and
   a central processing unit structured to move indicia displayed on the non-backlit video display in response to the position of the viewer.
9. The animal habitat according to claim 8, wherein the central processing unit is structured to respond to a presence of more than one viewer.

10. The animal habitat according to claim 9, wherein the central processing unit is structured to cease moving the indicia if more than one viewer is present.

11. The animal habitat according to claim 9, wherein the central processing unit is structured to designate a primary viewer, to move the indicia in response to movements of the primary viewer, and to ignore positions and movements of other viewers.

12. The animal habitat according to claim 9, wherein the central processing unit is structured to calculate an average viewer position and to move the indicia in response to the average viewer position.

13. A method of displaying an object, comprising:
providing a display case, the display case having:
- a non-backlit video display screen forming a front of the display case;
- a light source within the display case;
- a switchable LCD film disposed on a back surface of the non-backlit video display; and
- means for selectively supplying power to the switchable LCD film; and selectively applying and removing power to the switchable LCD;

whereby viewing of the object through the non-backlit video display, as well as reading indicia displayed on the video display screen, are possible when the light source is lit and the switchable LCD film has power applied, and viewing indicia displayed on the video display screen, but not viewing the object through the display screen, are possible when no power is applied to the switchable LCD film.

\* \* \* \* \*